(12) United States Patent
Melsheimer

(10) Patent No.: US 10,973,525 B2
(45) Date of Patent: Apr. 13, 2021

(54) VAGINAL POSITIONER FOR UTERINE TAMPONADE DEVICE AND METHODS OF USING THE SAME

(71) Applicant: Cook Medical Technologies LLC, Bloomington, IN (US)

(72) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 179 days.

(21) Appl. No.: 16/123,433

(22) Filed: Sep. 6, 2018

(65) Prior Publication Data

US 2019/0110797 A1 Apr. 18, 2019

Related U.S. Application Data

(60) Provisional application No. 62/573,463, filed on Oct. 17, 2017.

(51) Int. Cl.
*A61B 17/12* (2006.01)
*A61B 17/42* (2006.01)
(Continued)

(52) U.S. Cl.
CPC .... *A61B 17/12136* (2013.01); *A61B 17/1204* (2013.01); *A61B 17/42* (2013.01); *A61B 2017/00557* (2013.01); *A61B 2017/12004* (2013.01); *A61B 2017/4216* (2013.01); *A61B 2217/005* (2013.01); *A61M 25/04* (2013.01)

(58) Field of Classification Search
CPC .......... A61B 17/1204; A61B 17/12136; A61B 17/42; A61B 2017/00557; A61B 2217/005; A61B 17/0057; A61B 2017/1205; A61B 2017/12004; A61B 17/4216; A61B 17/4225; A61M 25/04; A61F 2/2442;
(Continued)

(56) References Cited

U.S. PATENT DOCUMENTS 837,085 A 11/1906 Loar
3,822,702 A 7/1974 Bolduc
(Continued)

FOREIGN PATENT DOCUMENTS

DE 4225520 A1 2/1994
JP 2014100303 A 6/2014
WO WO 00/57943 A1 10/2000

OTHER PUBLICATIONS

Search Report and the Written Opinion for PCT/US2019/051100, dated Feb. 11, 2020, 18 pages.
(Continued)

*Primary Examiner* — Ashley L Fishback
*Assistant Examiner* — Uyen N Vo
(74) *Attorney, Agent, or Firm* — Brinks Gilson & Lione

(57) ABSTRACT

A device for use with a uterine tamponade apparatus, such as the Bakri® postpartum hemorrhage balloon, is disclosed. The device comprises an anchor for deployment within the vagina to securely retain the balloon in its proper position within the uterine cavity, allowing the balloon to function as intended for the control and management of postpartum hemorrhage and uterine bleeding. Methods of use of the vaginal anchor are also disclosed.

28 Claims, 6 Drawing Sheets

(51) Int. Cl.
*A61M 25/04* (2006.01)
*A61B 17/00* (2006.01)

(58) Field of Classification Search
CPC .... A61F 2/2445; A61F 2/2403; A61F 2/2409; A61F 2/2427; A61F 2/2466; A61F 2220/0025
See application file for complete search history.

(56) References Cited

U.S. PATENT DOCUMENTS

| | | |
|---|---|---|
| 4,207,891 A | 6/1980 | Bolduc |
| 4,601,698 A | 7/1986 | Moulding |
| D286,677 S | 11/1986 | Osborne |
| 4,753,640 A | 6/1988 | Nichols et al. |
| 4,964,854 A | 10/1990 | Luther |
| 5,295,968 A | 3/1994 | Martel et al. |
| 5,569,222 A | 10/1996 | Haselhorst et al. |
| 6,245,029 B1 | 6/2001 | Fujita et al. |
| 6,395,012 B1 | 5/2002 | Yoon et al. |
| D476,418 S | 6/2003 | Sprieck |
| 6,740,095 B2* | 5/2004 | Watson, Jr. .......... A61B 17/122 606/120 |
| 6,813,520 B2 | 11/2004 | Truckai |
| D565,192 S | 3/2008 | Tajima |
| D585,547 S | 1/2009 | Bisleri |
| D630,733 S | 1/2011 | Ahlgren |
| D640,785 S | 6/2011 | Lee |
| D663,832 S | 7/2012 | Essinger |
| 8,282,612 B1 | 10/2012 | Miller |
| 8,287,496 B2 | 10/2012 | Racz |
| 8,323,278 B2* | 12/2012 | Brecheen .......... A61B 17/4241 606/45 |
| D692,134 S | 10/2013 | Lee-Sepsick |
| D699,341 S | 2/2014 | Clark |
| 8,770,200 B2* | 7/2014 | Ahluwalia .................. 128/830 |
| D713,957 S | 9/2014 | Woehr |
| 9,028,401 B1* | 5/2015 | Bacich .............. A61M 25/1003 600/204 |
| 9,067,013 B2 | 6/2015 | Wright et al. |
| D747,802 S | 1/2016 | Freigang |
| D748,777 S | 2/2016 | Uenishi |
| D751,704 S | 3/2016 | Corydon |
| 9,364,638 B2 | 6/2016 | Duncan |
| D772,411 S | 11/2016 | Heath |
| D798,446 S | 9/2017 | Nino |
| D816,217 S | 4/2018 | Naughton |
| D846,116 S | 4/2019 | Naughton |
| D854,148 S | 7/2019 | Prinz |
| D859,651 S | 9/2019 | Harding |
| 2004/0030352 A1 | 2/2004 | McGloughlin et al. |
| 2005/0143689 A1 | 6/2005 | Ramsey, III |
| 2005/0256532 A1* | 11/2005 | Nayak ................ A61B 17/0057 606/151 |
| 2006/0015075 A1 | 1/2006 | Blanco |
| 2006/0173486 A1 | 8/2006 | Burke et al. |
| 2009/0157007 A1 | 6/2009 | McKinnon |
| 2010/0106163 A1* | 4/2010 | Blair .................. A61B 17/4241 606/119 |
| 2011/0060317 A1 | 3/2011 | Frojd |
| 2011/0220120 A1 | 9/2011 | Frigstad et al. |
| 2011/0259344 A1* | 10/2011 | Ahluwalia ............ A61B 90/04 128/834 |
| 2013/0204208 A1 | 8/2013 | Olson et al. |
| 2014/0094773 A1 | 4/2014 | Lampropoulos |
| 2014/0158138 A1 | 6/2014 | Ziv et al. |
| 2015/0051634 A1 | 2/2015 | Kravik et al. |
| 2015/0202411 A1* | 7/2015 | Duncan ................ A61B 17/42 604/544 |
| 2015/0342641 A1 | 12/2015 | Belfort et al. |
| 2016/0045719 A1 | 2/2016 | Ha et al. |
| 2016/0100861 A1* | 4/2016 | Parys .................... A61B 17/42 600/249 |
| 2016/0106466 A1 | 4/2016 | Gruber et al. |
| 2016/0166282 A1 | 6/2016 | Juravic et al. |
| 2016/0256301 A1 | 9/2016 | Roeder |
| 2017/0312432 A1 | 11/2017 | Huang |
| 2018/0360494 A1 | 12/2018 | Melsheimer |
| 2019/0059947 A1 | 2/2019 | Bunch et al. |
| 2019/0110797 A1 | 4/2019 | Melsheimer |

OTHER PUBLICATIONS

Partial International Search Report for PCT/US2018/036865, dated Aug. 31, 2018, 10 pages.
International Search Report and Written Opinion for PCT/US2018/036865, dated Oct. 23, 2018, 18 pages.
International Preliminary Report on Patentability and Written Opinion for PCT/US2018/036865, dated Dec. 24, 2019, 8 pages.
Invitation to Pay Additional Fees and Communication Relating to the Results of the Partial International Search for PCT/US2019/051100, dated Dec. 16, 2019, 11 pages.
Examination Report for Australian Application No. 2018288595, dated Apr. 20, 2020, 5 pages.

* cited by examiner

VAGINAL POSITIONER FOR UTERINE TAMPONADE DEVICE AND METHODS OF USING THE SAME

RELATED APPLICATIONS

This application claims the benefit of the filing date under 35 U.S.C. § 119(e) of Provisional U.S. Patent Application Ser. No. 62/573,463, filed Oct. 17, 2017, which is hereby incorporated by reference.

TECHNICAL FIELD

The present invention relates generally to an apparatus and methods for controlling uterine bleeding, and more specifically, to a device for use with a uterine tamponade assembly that facilitates proper positioning and retention of the tamponade assembly within the uterus.

Uterine bleeding is a clinical condition attributable to a variety of causes, including postpartum hemorrhages (PPH) following vaginal and/or cesarean childbirth. Postpartum hemorrhage or excessive blood loss after birth is commonly caused by uterine atony whereby the uterus fails to contract normally after the delivery of a baby, leading to continuous bleeding. If left untreated, PPH may cause serious complications or even death.

There are a variety of techniques used for treating and managing PPH, including the administration of muscle contracting drugs or agents alone or in combination with other mechanical or surgical techniques. One such technique includes inserting a tamponade apparatus, such as a balloon catheter into the uterus, wherein the balloon is inflated to a sufficient pressure and volume until it conforms generally to the contour of the uterine cavity. The application of pressure to the interior uterine wall provides a tamponade effect until bleeding is controlled or stopped. One example of a uterine tamponade balloon catheter is the Bakri® balloon, Cook Medical Technologies LLC, Bloomington, Ind. The effectiveness of the Bakri® balloon may be partially attributable to maintaining the balloon in a proper position within the uterine cavity, and more specifically, in the lower uterine segment.

In most cases, the balloon stays in place in the uterus during treatment as long as the balloon was inserted properly. However, in some instances, the uterus may try to "deliver" or expel the balloon through an insufficient or dilated cervix and into the vagina, thereby requiring the balloon to be deflated and reinserted. Thus, it is desirable to prevent full or partial dislodgement of the balloon from the uterus by providing a device located in the vagina which anchors the balloon catheter in a desired position within the uterus. Accordingly, the disclosed device can be used with various known uterine tamponade devices, such as the Bakri® balloon. The disclosed device may be deployed within the vagina to securely retain the balloon in its proper position within the uterine cavity, allowing the balloon to function as intended for the control and management of PPH and uterine bleeding.

SUMMARY

The present disclosure provides an apparatus and method for securely anchoring a uterine tamponade device in its proper position within the uterine cavity. In one example, a uterine tamponade assembly is disclosed. The assembly comprises a catheter comprising a longitudinal body having a proximal end and a distal end and at least one drainage lumen extending there between. An expandable tamponade device is located at the distal end of the catheter, the tamponade device configured for insertion into the body cavity. The assembly further comprises an anchor for securing the assembly within the body cavity, the anchor includes a clip, a first arm extending radially outwardly from the clip, and a resilient outer disk disposed about the clip. The first arm is secured to the outer disk.

The present disclosure also provides for a vaginal anchor for securing a balloon catheter in the uterine cavity. In one example, the anchor comprises a clip and a first arm extending radially outwardly from the clip. A resilient outer disk is disposed about the clip and the first arm is secured to the outer disk.

DETAILED DESCRIPTION

Throughout this specification, the terms proximal and proximally are used to refer to a position or direction away from, or even external to a patient's body and the terms distal and distally are used to refer to a position or direction towards the patient and/or to be inserted into a patient's body orifices or cavities. The embodiments described below are primarily in connection with a device for use with, or as an accessory to, a tamponade device such as a balloon catheter for treating postpartum hemorrhage, and for anchoring the balloon catheter in a desired position within the uterus. However, the described device may also be used in connection with a range of medical instruments which are inserted into various body cavities to maintain the position of such instruments depending on the technique or procedure being performed as will be appreciated by those of skill in the art.

Figure 1:
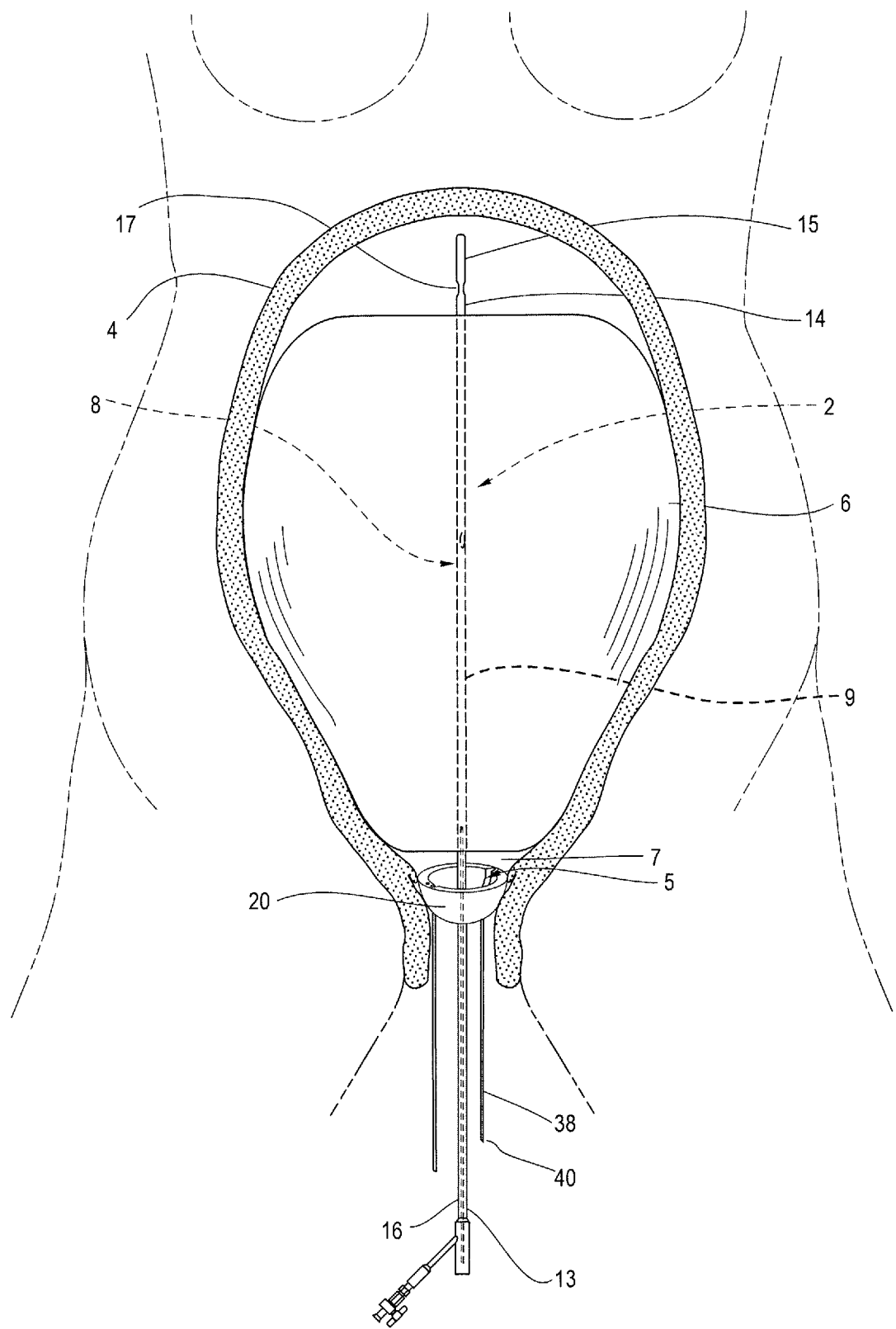
FIG. 1 is a front view of a patient's anatomy showing a uterine tamponade device and one example of an anchor deployed in the vagina for anchoring the tamponade device in place within the uterine cavity.

FIG. 1 illustrates one example of a uterine tamponade assembly 2 positioned within a patient's anatomy. Tamponade, which is the closure or blockage of a wound by applying direct pressure to the source of bleeding, is a useful method of stopping or managing bleeding or hemorrhage. One example of a known tamponade assembly includes a Bakri® balloon catheter (Cook Medical Technologies LLC, Bloomington, Ind.). The tamponade assembly 2, i.e., Bakri® balloon catheter, is shown as being expanded within the uterine cavity and is shown as being equipped with a retention device or anchor 12 deployed in the vagina 5 for anchoring the balloon catheter 2 in place within the uterine cavity 4. While the balloon catheter 2 is intended for placement in the uterine cavity 4 of a patient for treating and controlling postpartum hemorrhage (PPH), it may also be used in various other locations, lumens or orifices within the body, including vessels, bones, organs or other tissues, as necessary or desired. Its dimensions are alterable so that it may be appropriately dimensioned to navigate to the uterus 4, or any other target body cavity, from which fluid, such as blood, will be drained.

As shown in FIG. 1, the tamponade assembly 2 preferably includes a catheter 8 having a longitudinal shaft 9 and a distal end 15 and a proximal end 13. There is a drainage lumen 16 extending along the length of the longitudinal shaft 9 between the proximal 13 and distal 15 ends and, in one example, a connector (such as a Y-connector or any other suitable connector) may be located at the proximal end 13 of the catheter 8 for connecting the catheter to a collection bag or receptacle for receiving fluid and/or blood drained from the patient. The catheter 8 may include one or more openings 17 at or near its distal end 15, such that when the distal end 15 of the catheter 8 is positioned in the uterus 4, the openings 17 allow blood and other fluids to enter and flow through the drainage lumen 16. The drainage lumen may also be used to introduce irrigation fluid or other material into the uterus, such as to flush the openings 17 at the distal end 15 of the catheter 8 should they become blocked with clotted blood, tissue or other debris. The catheter 8 may also include additional ports or orifices at various points along the longitudinal shaft 9 to allow blood or other fluid to enter the catheter 8.

A tamponade device 6, such as a balloon, is located near the distal end 15 of the catheter 8, and is preferably made of an expandable material such as rubber, silicone, latex or any other expansible biocompatible material. Other tamponade mechanisms may also be used in lieu of or in addition to the balloon 6, such as plurality of arms, tubes, loops, mesh or similar structures capable of expanding or otherwise conforming to the uterine cavity 4. An inflation lumen 14 within the catheter 8 is provided to allow for inflation and deflation of the balloon 6. The inflation lumen 14 may run parallel with the drainage lumen 16, but preferably, the two lumens 16, 14 remain separate for their entire lengths. Various media, such as water, saline, air or other physiologically compatible medium may be introduced through the inflation lumen 14 to facilitate controlled expansion of the balloon 6.

Once the balloon 6 has been placed within the uterus 4 of the patient, the balloon 6 may be inflated or otherwise expanded. Preferably, the balloon 6 has sufficient compliance such that, when expanded, it conforms generally to the shape and contour of the cavity in which it is placed, and when deflated, can be sufficiently reduced in profile to provide for easy insertion and removal through the cervix 7 and vagina 5. The size and volume to which the balloon 6 may expand is preferably determined by the body cavity where hemorrhage control is needed. As shown in FIG. 1, the balloon 6 is preferably inflated with a sufficient volume and pressure such that it conforms generally to the contours of the uterine cavity 4, and more specifically, to the lower uterine segment. In one example, when using a balloon 6 such as the Bakri® balloon, the balloon 6 may be inflated with up to about 500 ml of saline. In other examples, if other types or sizes of balloons are used, the inflation volume may be more or less. The inflated balloon 6 then exerts a generally uniform compressive force or pressure upon the uterine wall to substantially reduce or even stop the uterine bleeding or hemorrhage. It may also be possible to coat or impregnate all or at least a portion of the balloon surface that comes into contact with the uterine wall with biocompatible materials, drugs or other substances that may enhance or assist in controlling uterine bleeding. In one non-limiting example, this may include muscle contracting or clotting enhancing drugs or other substances that facilitate inflation/deflation of the balloon 6.

As shown in FIG. 1, the catheter 8 may further include an internal stylet 10 to provide structure or added rigidity to the catheter 8. The stylet 10 may be integrally formed within the catheter or, alternatively, the stylet 10 may be inserted into the catheter 8 by a physician prior to or during use. Preferably, the stylet 10 extends longitudinally within the drainage lumen 16, or alternatively through the inflation lumen 14 or through an additional or separate lumen. In one non-limiting example, the internal stylet 10 may be a hollow vinyl tube with a lumen extending there through, which provides an additional drainage conduit through which blood or other fluids can flow. However, the stylet 10 may be a variety of other shapes and configurations, solid or hollow, and made of suitable biocompatible materials including plastics, metals and/or combinations thereof. The stylet 10 may run the entire length, or at least a portion of the length of the catheter 8, and extend to a location adjacent to or just distal of the openings 17 at the distal end 15 of the catheter 8, for example, or at least extend a sufficient length so as to add longitudinal stability to the catheter 8. The stylet 10 thereby reduces or substantially eliminates unwanted folding and/or bending of the catheter 8, while also resisting and preventing longitudinal shortening, shrinkage and/or collapse during trans-vaginal insertion (and/or insertion through C-section) and during positioning of the balloon 6 within the uterus 4.

Figure 2:
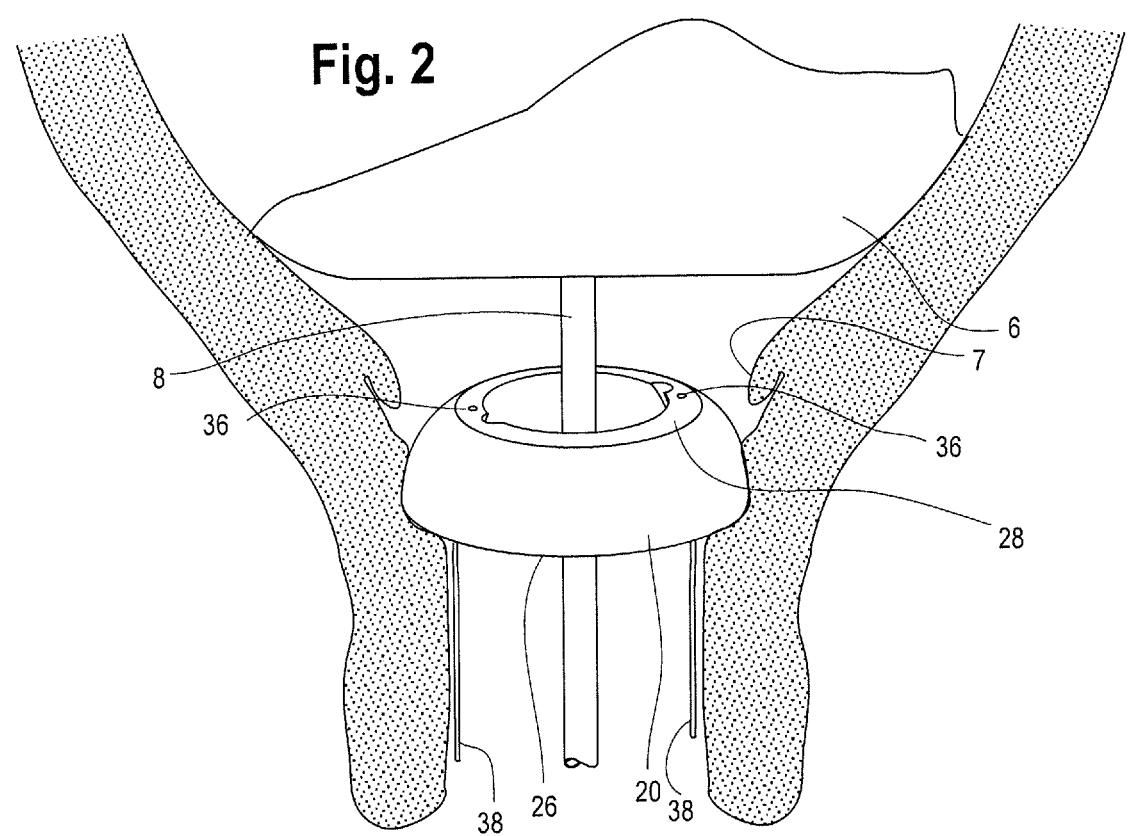
FIG. 2 is an enlarged perspective view of one example of an anchor secured to a catheter shaft and deployed in an alternate orientation in the vagina with multiple tethers extending out of the body.
Figure 10:
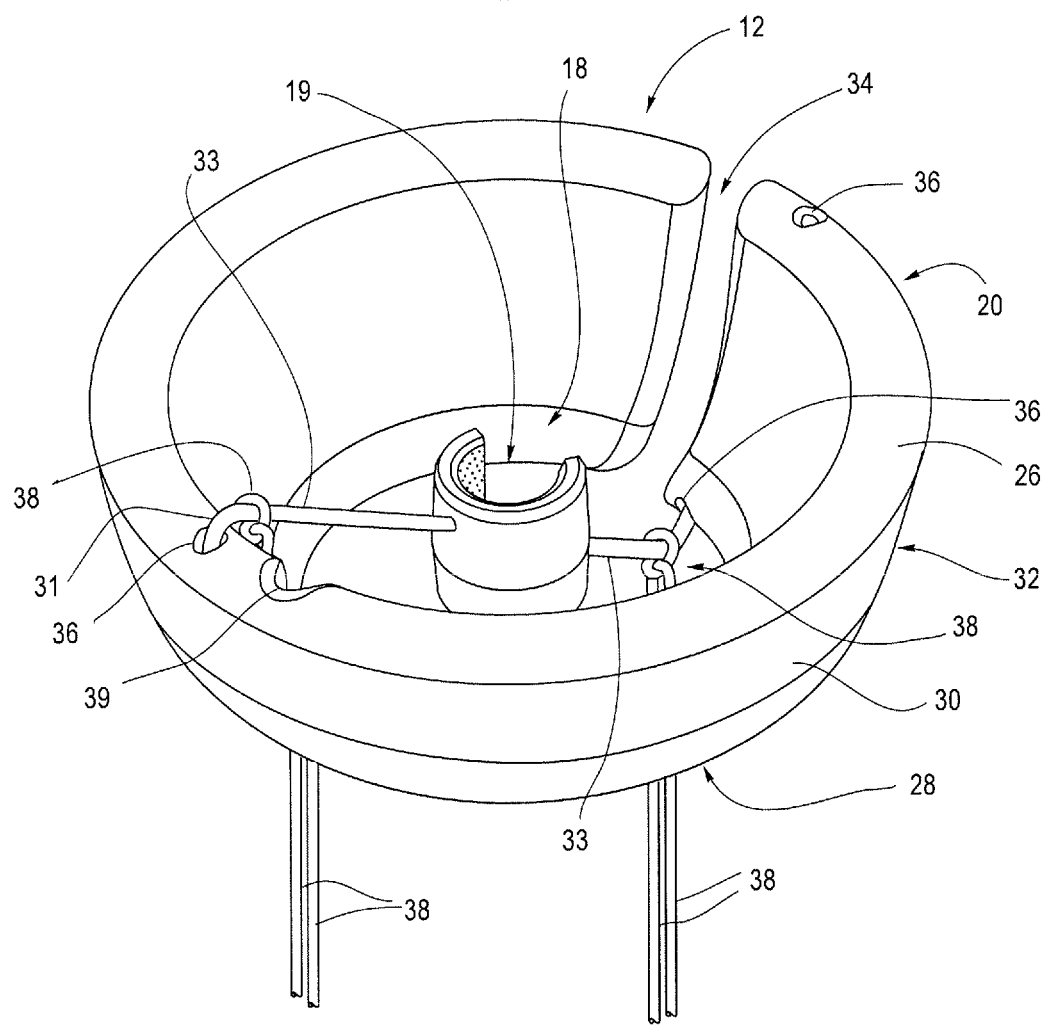
FIG. 10 is a perspective view of another example of an anchor including a slit in the outer disk to allow the anchor to be snap-fitted onto a catheter shaft.

As illustrated generally in FIGS. 1 and 2, the assembly 2 includes a device to facilitate retention of the assembly 2 and prevent unintentional or unwanted dislodgement once the balloon 6 has been properly positioned and expanded within the uterus 4. In one example, the device is a retention mechanism such as anchor 12. The anchor 12 is preferably usable in connection with the balloon catheter assembly 2, and may be provided as an accessory thereto. It is also contemplated that the anchor 12 may be used in connection with other medical devices in which it is desirable to retain such devices in a particular position or location within a body cavity. As such, the anchor 12 is preferably removably attachable to the assembly 2 so that it can be attached or secured to the catheter 8 when needed, and also conveniently removed if desired. In one example, the anchor 12 can be threaded on to the longitudinal catheter shaft 9 at a desired location. In another example, the anchor 12 may be snap-fitted onto the longitudinal catheter shaft 9 at a desired location or otherwise removably attached such as by friction fit, adhesive or other suitable attachment mechanisms, while allowing the anchor 12 to remain slideably movable along the longitudinal shaft 9 of the catheter 8. One example of an anchor 12 that can be snap-fitted onto the catheter shaft 9 is illustrated in FIG. 10. As shown there, the outer disk 20 may comprise a slit or opening 34 to accommodate the catheter shaft 9 allowing the anchor to snap on to the shaft 9 at any desirable location.

Figure 3A:
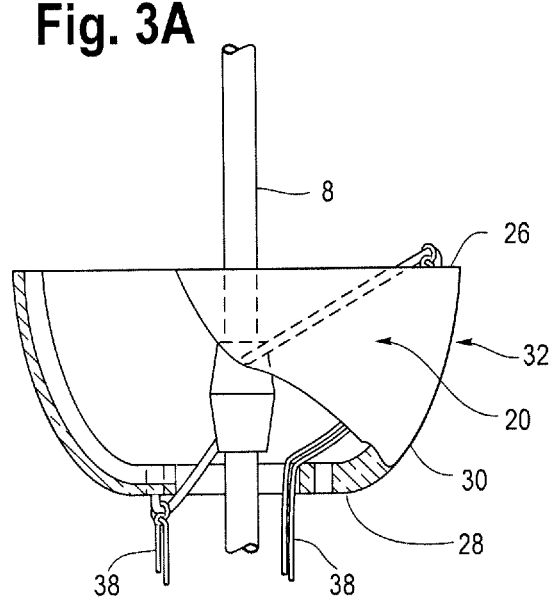
FIG. 3A is a partial cut-away view of one example of the anchor shown in FIG. 1.
Figure 3B:
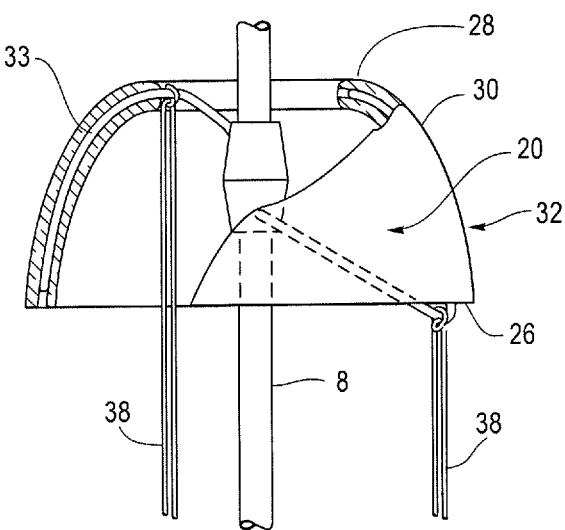
FIG. 3B is a partial cut-away view of one example of the anchor shown in FIG. 2.
Figure 6:
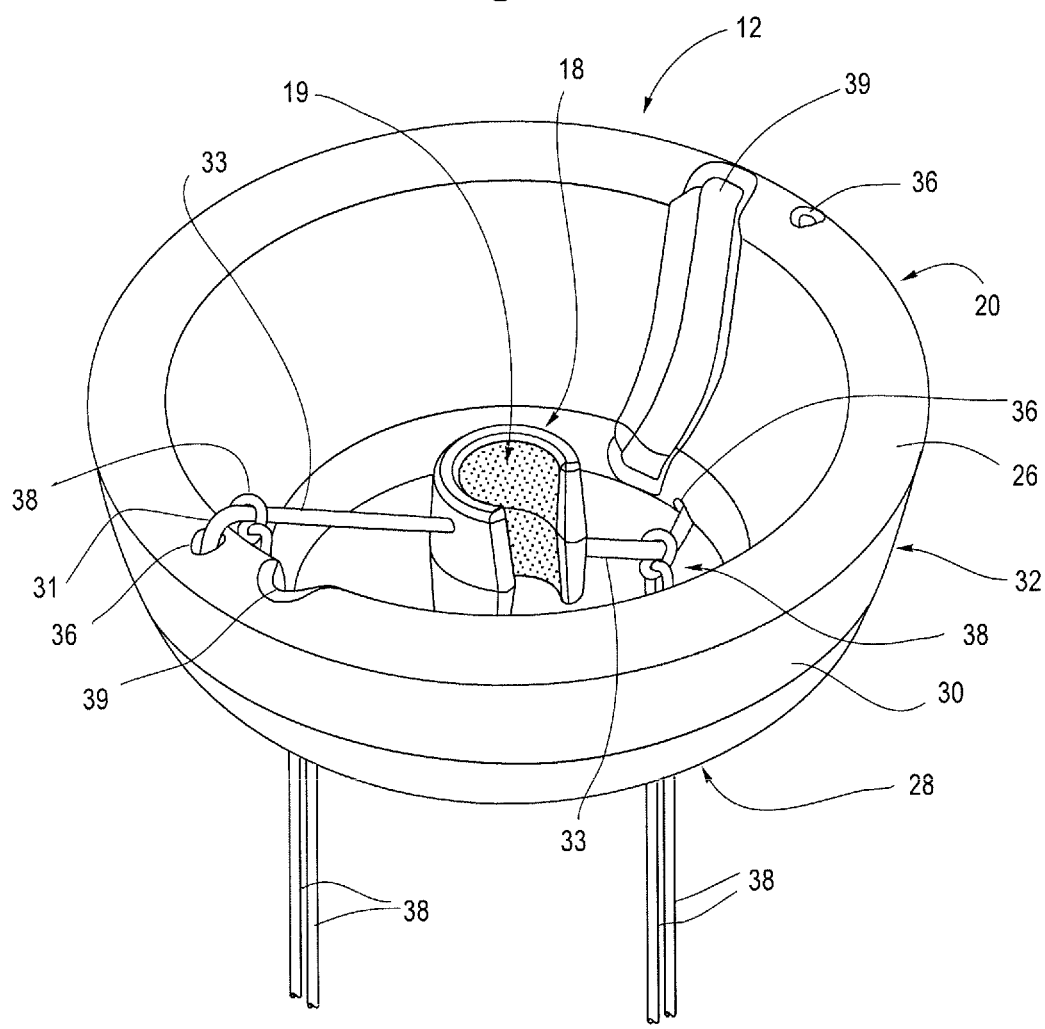
FIG. 6 is top perspective view of the anchor of FIG. 1 showing details of the inner components including an inner clip and internal framework and one example of a hinge structure.
Figure 7:
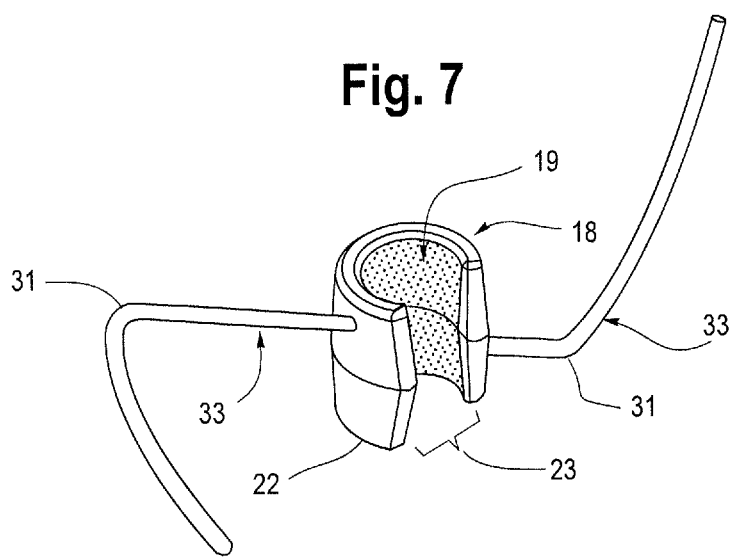
FIG. 7 is perspective view of one example of an inner clip and internal framework of the anchor.
Figure 8:
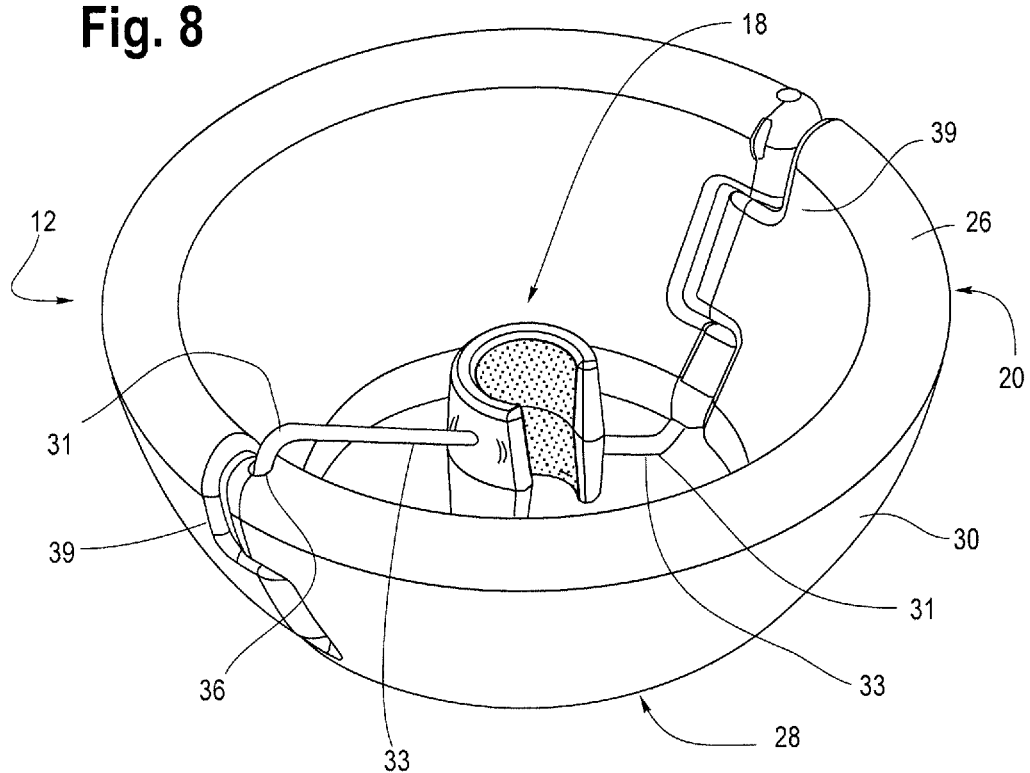
FIG. 8 is a top perspective view of an anchor with another example of a hinge structure.

As shown generally in FIGS. 3, 6 and 8, in one embodiment, the anchor 12 may comprise an inner clip 18 and an outer bowl or disk 20. In one example, the inner clip 18 may be relatively rigid compared to the outer disk 20. For example, the inner clip 18 may be made of a relatively harder and/or more rigid plastic, including but not limited to ABS, nylon and/or polyurethane blends and/or polycarbonate. The clip 18 may be a ring-like structure that fully surrounds or encircles the shaft 9 of the catheter 8 and can be threaded onto one end of the catheter 8 and pushed longitudinally or slid into position at a desired location on the catheter 8 for use. Alternatively, the clip 18 may fully or at least partially surround the shaft 9 of the catheter. For example, as shown in FIG. 7, the clip 18 may comprise a generally ring-like "c-clip" structure with opposing facing or abutting arms that form a small opening or slot 23 between the opposing facing arms that allows the clip 18 to be snap fitted on (and off) of the catheter 8 from the side at any desirable location along the length of the shaft 9 of the catheter 8. In one example, the clip 18 may be constructed of a material that is rigid enough to allow the clip to maintain its overall structure and form to snugly fasten onto the catheter, but flexible enough to allow the opposing facing arms to be pulled or moved apart far enough to receive the longitudinal body 8 of the catheter 9 there between during attachment and removal of the anchor 12 from the catheter 9. However, in a resting position, the natural resiliency of the opposing facing arms of the inner clip 18 may result in the anus pulling slightly radially inwardly such that the arms are adjacent, abutting or even touching to form a substantially circular structure. The inner clip 18 may also comprise a horseshoe shape or semi-circular or curved shape that allows the inner clip 18 to be removably attached to the catheter 8.

In one example, the inner diameter of the clip 18 may be in the range of approximately 0.1 in. to 1.5 in., and more preferably about 0.3 in. in order to wrap snugly around the outer diameter of the longitudinal shaft 9 of the catheter 8. However, it is also contemplated that the inner diameter of the clip 18 may be modified to a variety of shapes and dimensions so as to be usable and compatible with other sizes and diameters of catheter tubing or any other device to which it may be desirable to attach the clip 18. As shown in FIG. 7, the clip 18 has a first end 21 and a second end 22 and a center opening 19. The clip 18 may have a smooth outer edge or surface and a roughened or textured inner surface 11 of the center opening 19 that serves to reduce or prevent slippage or dislodgment of the clip 18 on the longitudinal shaft 9 of the catheter 8. In one example, the roughened inner surface 11 may aid placement of the anchor 12 by including a textured design or pattern that glides smoothly when pushed up or distally into place on the shaft 9 of the catheter 8, but which resists sliding in the opposite (proximal) direction during use to enhance traction along the shaft 9, providing retention of the anchor 12 and preventing unwanted sliding or dislodgement of the anchor 12.

In addition to the inner clip 18, the anchor 12 may further include an outer disk 20 having a first end 26, a second end 28 and a sidewall 30 extending there between. The disk 20 is generally shaped and configured to have a center opening 24 which surrounds or covers at least a portion of the inner clip 18. The inner diameter of the second end 28 of the outer disk 20 may be between about 2 cm and 5 cm and more preferably 3.5 cm, while the first end 26 of the outer disk 20 may have a flared portion 32 having an outer diameter of between about 5 cm and 10 cm and more preferably 7 cm. The outer diameter of the clip 18 may be about 7 cm or less, or at least a small enough outer diameter so as to fit within the center opening 24 of the outer disk 20. As shown in FIG. 6, the clip 18 would be generally housed within the center opening 24 of the outer disk 20.

The material thickness of the disk 20 may be about 0.25 in. or 2-4 cm in order to provide sufficient flexibility and pliability to accommodate different and changing diameters of the vaginal canal following childbirth yet also provide enough strength to hold the balloon in place within the uterus. For example, as shown in FIGS. 1 and 2, the natural resiliency of the disk 20 allows the disk 20 to expand radially outwardly enough to securely maintain the anchor 12 in place in the vagina 5. As the birth canal contracts back down, the disk 20 can adjust in size to also contract, therefore allowing the anchor 12 to function efficiently and accurately as intended throughout the entirety of a procedure as the dimensions of the patient's anatomy changes. As such, the anchor 12 can be used to retain the tamponade assembly 2 in place across a wide range of patients having differing anatomical dimensions as well as within the same patient when the cervix 7 and vagina 5 change in size immediately following childbirth.

In one example, the disk 20 may be constructed of a material that can conform to the shape, size and configuration of the orifice in which it is to be placed, including the vaginal canal 5. The disk material is preferably biocompatible and pliable enough to expand and contract with the vaginal wall but rigid enough to retain its general shape and position inside of the vaginal canal. In one example, the disk 20 may be constructed of injection molded elastomeric polymer such as silicone with a durometer of about 30 D to about 70 D as necessary or desired. The disk 20 may also be constructed of other materials or soft plastics, rubbers, polymers and co-polymers and preferably a material that is relatively soft and/or pliable enough such that it is non-traumatic to the sensitive tissue of the cervix 7 and vagina 5, yet can maintain its overall structure in order to retain the tamponade assembly in position within the uterus 4.

In one example, the disk 20 may be an uninterrupted ring that fully surrounds and is coaxial with the inner clip 18. However, as previously mentioned, the outer disk 20 may include a slit or opening 34 that is positioned adjacent to or otherwise generally aligned with any slot 23 or gap formed in the ring-like structure of the inner clip 18. This allows the anchor 12, including the inner clip 18 and outer disk 20 to be snap fitted onto the longitudinal shaft 9 of the catheter 8 together as a unit as shown in FIG. 10. The first end 26 of the disk 20 may have a flare that extends radially outwardly, such that a flared proximal portion or end 32 of the disk 20 has an outer diameter of about 10 cm to about 15 cm. In one example, the flared portion 32 at the first end 26 of the disk 20 may be advantageous to aide in retention of the anchor 12 within the vagina 5. Preferably, the disk 20 has a smooth outer surface with generally rounded or curved edges to aide in patient comfort during insertion and removal from the vaginal canal 5.

Figure 4:
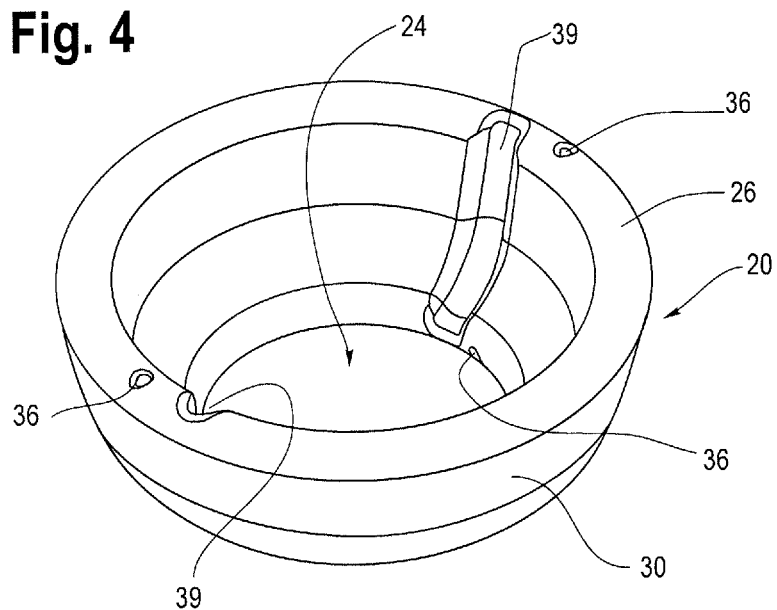
FIG. 4 is a top perspective view of one example of the anchor of FIG. 1 in a radially-outward deployed configuration and excluding any inner components.
Figure 9:
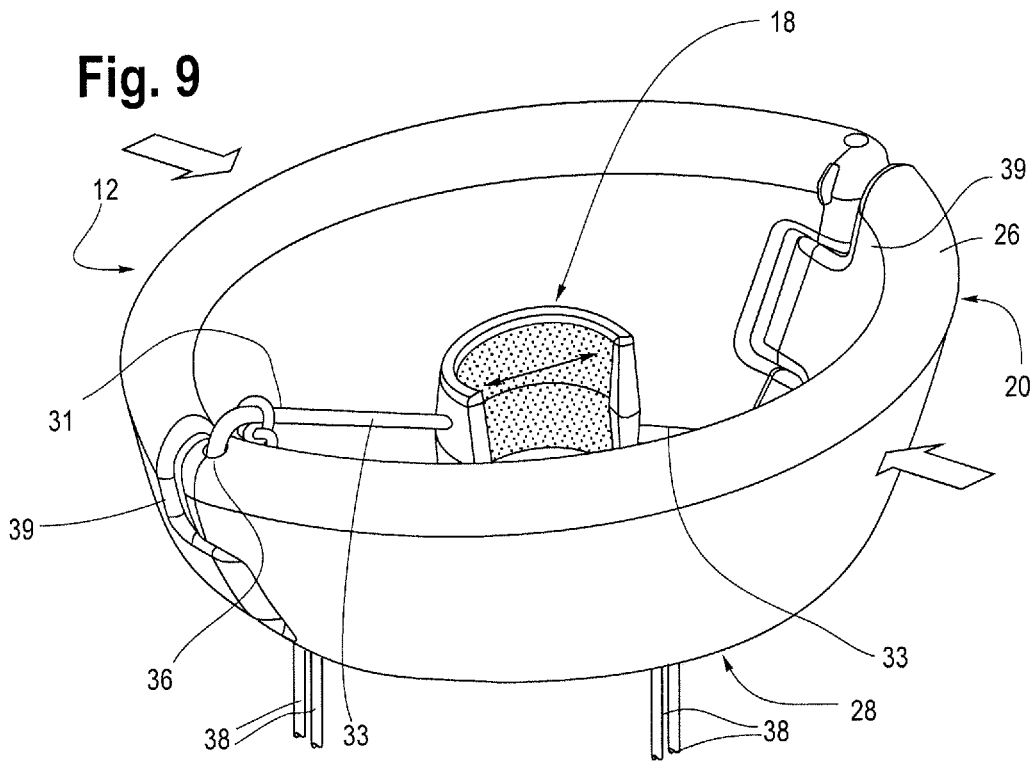
FIG. 9 is a top perspective view of the anchor of FIG. 8 with part of the internal framework removed showing hinge movement.

As shown in FIG. 4, the disk 20 may further include one or more openings or holes 36 formed therein. The one or more holes 36 may be formed in both the first end 26 and the second end 28 of the disk 20. In one example, there may be two holes, three holes or more holes formed in the disk, and in FIG. 4, there are four holes 36 formed in the disk (only three of which are visible due to the perspective view). The holes 36 are generally formed in the disk 20 equally spaced circumferentially around the first end 26 and the second end 28 of the disk 20 such that the holes are generally axially opposed from each other. Each of the holes 36 are configured to receive at least one arm 33 that extends radially outwardly from the inner clip 18 as shown in FIG. 9. However, as shown in FIG. 8, it is contemplated that at least two arms 33 extend radially outwardly from the inner clip 18 to form an inner supportive framework for the anchor 12. In one example, the framework provided by the at least two arms 33 may function to open the slot of the inner clip 18 when the disk 20 is squeezed during placement or removal. Conversely, the framework provided by the at least two arms 33 may also serve to keep the clip 18 tightly clamped onto the underlying catheter shaft 9 when the disk 20 returns to its expanded or naturally rounded shape.

At least one of the arms may extend from the inner clip 18 towards the first end 26 of the disk, while another arm may extend from the inner clip 18 towards the second end of the disk. As shown in FIGS. 6-9, a bend 31 in the arms 33 allows the arm to extend into and be received within at least one of the holes 36 formed in the outer disk 20. By providing a set of two opposing holes 36 in the first end 26 of the disk and another set of opposing holes in the second end 28 of the outer disk 20, the inner clip 18 can be oriented in any position and the outer disk 20 can still accommodate and receive the two arms 33 extending outwardly from the inner clip 18. In other words, the inner clip 18 can be oriented with the first end 21 of the clip 18 facing towards the first end 26 of the disk or it can be oriented with the first end 21 of the clip 18 facing towards the second end 28 of the disk 20. In either orientation, a hole 36 will be available in the outer disk to receive a portion of each arm 33 extending outwardly from the inner clip 18, as shown generally in FIGS. 3A and 3B. As such, one or more of the holes 36 that do not receive at least one of the arms 33 may remain unoccupied as shown in FIG. 6.

One or more lanyards or tethers 38 may be tied to the one or more awls, as shown generally in FIG. 6. The tethers 38 are long enough to extend outside of the body during use to allow the physician to comfortably and securely grasp the proximal ends 40 of the tethers 38 during removal of the anchor 12 from the vagina 5 upon completion of treatment as described in further detail below. More specifically, one tether 38 may be tied or otherwise secured to one arm 33 while a second tether 38 may optionally be tied or otherwise secured to another arm 33. The one or more tethers 38 may be tied or secured to any portion of the arm structures, however, as FIG. 6 illustrates, the tethers may be secured or knotted around the bent portion 31 of each arm 33. Attaching the tethers 38 to an internal structure of the anchor 12, such as the one or more arms 33 advantageously leaves the exterior of the anchor 12 smooth, to prevent discomfort, abrasion or tissue attachment.

Alternatively, the one or more tethers 38 may be tied or otherwise secured directly to the outer disk 20 itself. For example, one tether 38 may be threaded through one or more of the holes 36 formed in the wall of the outer disk 20 and tied or knotted to secure the tether 38 to the outer disk 20. A single tether 38 may be secured to the outer disk 20 through one of the holes 36, or additional tethers 38 may be secured to the outer disk 20 through any one of the additional holes 36 formed in the sidewall 30 of the outer disk 20. It is also contemplated that one or more tethers 38 can be tied or otherwise attached to the outer disk 20 in other acceptable and secure ways including, but not limited to adhesives, bonding, welding and/or other attachment mechanisms or methods. Preferably, the one or more tethers 38 are attached to the anchor 12 near or adjacent to one or more hinge structures 39 described in further detail below. When more than one tether 38 is present, the tether 38 which is lower-most or caudal is the only tether which is pulled to aid in removal of the device. When the tether 38 is pulled, it 1) tilts the outer disk 20 which causes the anchor it to lose its purchase between the vagina and cervix, 2) causes the outer disk 20 to elongate into a generally oval shape, causing the inner clip 18 to release its grip on the underlying catheter shaft 9, and 3) pulls the outer disk 20 from the patient's body because, when elongated, the generally oval shape of the outer disk 20 allows this atraumatic shape to be easily from the body.

The tethers 38 may be constructed of a material having enough strength to collapse at least a portion of the outer disk 20 to remove the disk 20 from the patient without risking breakage. In one non-limiting example, the tethers 38 may be constructed of a nylon monofilament, PTFE, Tevdek®, Polydek®, braided plastic fiber or like material to prevent stretching and breakage when the user pulls proximally on the tethers 38 during removal of the anchor 12 from the vagina 5. Preferably, the materials used to construct the anchor 12, including the inner clip 18 and outer disk 20, as well as the materials used to construct the tethers 38 may be transparent or semi-transparent in order to allow a physician to monitor blood flow that may be occurring behind the device within the cervix 7 and/or vagina 5. However, the inner clip 18 is small enough so as not to obscure visualization through the second end of the disk 20, so the inner clip 18, and/or other portions of the anchor 12 may be made of opaque or semi-opaque materials, if necessary or desired, while still providing adequate visualization to the physician.

When clipped on the catheter shaft 9 and slid into place within the vagina 5, the natural resiliency of the outer disk 20 of anchor 12 will allow the anchor 12 to move or deploy radially outwardly to its natural state and expanded dimension. As such, the anchor 12 will apply force to the vaginal wall, thus fixing the catheter shaft 9 and balloon 6 in place and substantially preventing dislodgement of the balloon 6 from the uterus 4. The one or more arms 33 that extend radially outwardly from the inner clip 18 provide structural integrity to the inside of the anchor 12 and may also simultaneously press inwardly upon the inner clip 18 as the vaginal canal presses inwardly upon the outer disk 20. Thus, in addition to the roughened texture 11 of the inner surface 19 of the clip 18, the additional inward force upon the inner clip 18 provided by the pressure from the vagina 5 and or cervix 7 upon the outer disk 20 via the one or more arms 33 further serves to snugly retain the clip 18 upon the catheter shaft 9 and prevent the clip 18 from unwanted sliding or moving from its desired position on the shaft 9.

Figure 5:
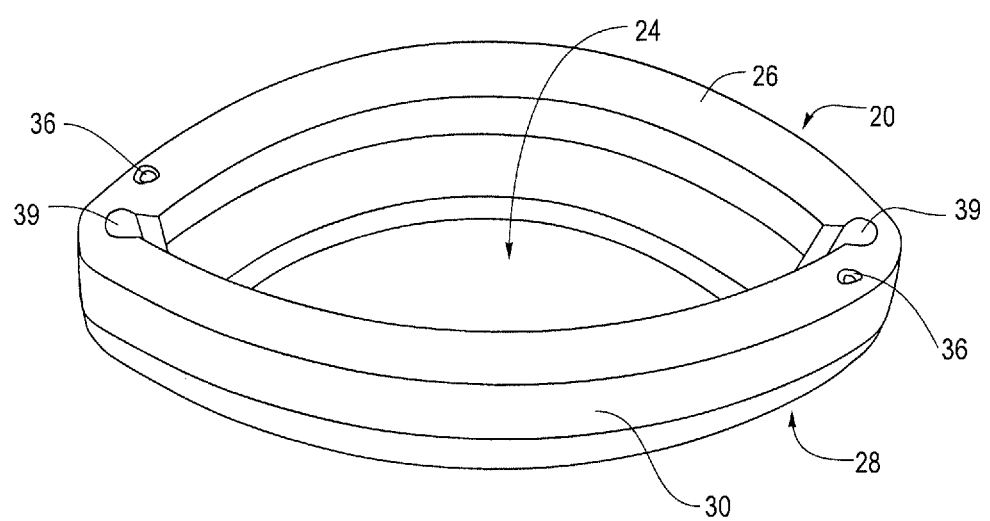
FIG. 5 is a top perspective view of the anchor of FIG. 4 in a collapsed configuration.

Further, as shown generally in FIGS. 4-6 and 8 and 9, the outer disk 20 may be collapsible and otherwise deformable to aid in removal from the cervix 7 and/or vagina 5. In one example, as shown in FIG. 4, the outer disk 20 may include one or more depressions or recesses formed in the wall of the outer disk 20. These recesses provide a portion of sidewall 30 of the outer disk 20 that has a reduced thickness such that the recesses may be more compliant or otherwise flexible so as to serve as a hinge structure 39. As shown in FIGS. 4, 5 and 6, the hinge structure 39 may be in the form of a living hinge or flexure bearing which may be a thinner area made from the same material as the surrounding pieces of the outer disk 20 that it connects. The reduced thickness of the recess allows the sidewall 30 to bend along the line of the hinge structure 39 with minimal friction and wear. This allows the outer disk 20 to move from a radially outwardly expanded position of FIGS. 4 and 6 to a folded or collapsed condition of FIG. 5 as the hinge structure 39 allows the sidewall 30 of the outer disk 20 to fold inwardly. When the outer disk 20 is in a collapsed condition as illustrated in FIG. 5, the anchor 12 may be more readily and comfortably removed from the cervix 7.

Similarly, in an alternative example, the outer disk 20 may comprise a hinge structure 39 that is in the form shown in FIGS. 8 and 9. The hinge structure 39 may comprise any one or more hinges recognized in the art including but not limited to a pivot hinge, continuous hinge, butt hinge, flag hinge, concealed hinge or any similar structure or mechanical bearing that allows the respective halves of the outer disk 20 to move or pivot relative to each other or otherwise allow the anchor 12 to fold or collapse to facilitate removal of the anchor 12 for the cervix. More specifically, as shown in FIGS. 8 and 9, the hinge structures 39 are generally spaced opposite each other about the periphery of the outer disk 20, allowing the anchor 12 be folded from a first generally rounded, outwardly expanded diameter shown in FIG. 8 to a second lower-profile oval shaped configuration as shown in FIG. 9. In one example, the outer ends of the one or more arms 33 that extend outwardly from the inner clip 18 may extend into, and be threaded through, the hinge structure 39 as shown in FIG. 8. In other words, the bend 31 in arm 33 allows the outer end of the arm 33 to extend through the hinge structure 39 and serve as a pivot point, hinge pin, pivot rod or axis of rotation about which the respective halves of the outer disk 20 move that are coupled or joined at the hinge structure 39, thus acting as a line of flexure.

Similarly, the outer end of one or more arms 33 may extend through one or more channels formed in, and extending through, the outer wall 30 of the outer disk. Hole 36 may form an opening to the channel in order to receive arm 33 therein, as shown, for example, in FIGS. 3A and 3B. One or more such channels may be formed in the wall 30 of the outer disk 20 next to or generally adjacent hinge structure 39. Because the outer disk 20 is formed from a resilient material, such as silicon rubber or polyurethane, for example, the outer disk 20 is generally biased in the first outwardly expanded diameter. Thus, when removal of the anchor 12 is desired, the anchor 12 can be manipulated in order for it to be collapsed about the hinge structure 39 as described in further detail below.

As previously noted, the rigidity provided to the catheter 8 by the internal stylet 10 prevents longitudinal collapse of the catheter 8, such that at least the portion of the catheter 8 located between the balloon 6 and the anchor 12 will maintain structural integrity and longitudinal length. This prevents longitudinal shrinkage or collapse of the longitudinal catheter shaft 9 when force is exerted on it in either a proximal and/or distal direction, such as in the event that the uterus 4 attempts to "deliver" the balloon 6 through an insufficient cervix 7 (thus exerting pressure on the catheter shaft 9 in a proximal direction) and/or when a physician pushes the catheter 8 into the uterus 4 during insertion (thus exerting pressure on the catheter shaft 9 in a distal direction).

Turning now to FIGS. 1 and 2, use and deployment of the anchor 12 with a uterine tamponade apparatus 2 such as the Bakri® balloon catheter may be as follows. In one example, the uterine tamponade assembly 2 is inserted into a patient and the balloon 6 is suitably positioned within the uterus 4. Optionally, the internal stylet 10 may be inserted into a lumen of the catheter 8, such as into the drainage lumen 16, either before, during or after inflation of the balloon 6. The distal end 15 of the catheter 8 carrying the tamponade balloon 6 may be inserted trans-vaginally through the cervix 7 (or alternatively inserted through a C-section incision) and into the uterus 4 of a patient in its deflated or radially contracted state. Once the balloon 6 is in its desired position in the uterus 4, it is inflated or otherwise expanded with a physiologically suitable fluid through the inflation lumen 14. The shape of the fully expanded balloon 6 will generally conform to the shape of the interior of the uterus 4, and preferably the lower uterine segment, thus exerting a compressive force against the uterine walls. The anchor 12 may be loaded on to the shaft 9 of the catheter 8 at any position along the shaft 9, such as by threading the anchor 12 on to one end of the catheter 8 or it may be snap-fitted onto the longitudinal catheter shaft 9 at a location that will, at least initially, remain outside of the patient.

The anchor 12 can then be moved along the shaft 9, such as by squeezing it into a generally oval shape, until it is adjacent to the balloon 6. After correct positioning of the balloon 6 is confirmed (and the balloon 6 inflated) the anchor 12 can be positioned adjacent to the cervix 7. In one example, as shown in FIG. 1, the anchor 12 can be placed in an orientation in which the first end 26 faces distally, such that the flared portion 32 of the outer disk 20 is facing the proximal balloon segment. However, it is also contemplated that the anchor 12 can be placed within the cervix 7 in an alternate orientation as represented by FIG. 2, in which the first end 26 of the anchor 12 is facing downwardly or proximally towards the opening of the vagina 5, as shown in FIG. 2. As such, the anchor 12 is designed and configured to be positioned within a patient in multiple orientations with equal success, comfort and efficiency. In other words, the rounded atraumatic shape and conforming materials provides for positioning of the anchor 12 without discomfort or trauma to the surrounding delicate tissues. This makes insertion and placement simple and straightforward while reducing risk of improper deployment.

Using the orientation shown in FIG. 1 as an illustrative example, the proximal flared portion or end 32 of the outer disk 20 will face distally, away from the physician performing the procedure. The physician may squeeze or pinch the sides of the outer disk 20, while also possibly tilting the anchor 12 at a slight angle relative towards the vaginal canal, while pushing the anchor 12 in a distal direction along the catheter shaft 9 up into the vaginal canal 5 until it has reached an area close to the opening of the cervix 7. This action provides tension on the internal framework provided by the one or more arms 33, thus causing the inner clip 18 to loosen its grip upon the longitudinal catheter shaft 9.

Once the physician has ensured that the anchor 12 has moved as far as necessary in a distal direction such that the anchor 12 is immediately adjacent to the lower (proximal) balloon segment, the physician may release their grip on the outer disk 20. Once the physician has released the outer disk 20 from a pinched configuration, the resiliency of the material of the outer disk 20 allows the disk to expand radially outwardly to its natural resting state to accommodate different and changing diameters of the vaginal canal following childbirth. As such, the anchor 12 is therefore adjustable and/or customizable, in that the outer disk 20 deploys radially outwardly a selected distance so that it can be adjusted to fit with a variety of vaginal diameters depending on a particular patient's anatomy and location of deployment. Expansion of the outer disk 20 will also allow the inner clip 18 to resume its grip upon the underlying catheter shaft 9. The roughened inner surface of the inner clip 18 also aids in the retention of the clip 18 in position upon the exterior surface of the longitudinal catheter shaft 9. Pressure from the inflated balloon 6 also serves to provide slight downward (proximal) pressure upon the cervix and vagina 5 thereby also helping to urge the outer disk 20 to flare outward and maintain its position within the vagina 5. The anchor 12 is therefore secured to the shaft 9 of the catheter 8, thus, maintaining the position of the inflated balloon tamponade device 2 in the uterus for a positive clinical outcome. The one or more tethers 38 will extend proximally from the outer disk 20 to a location outside of the body.

Once the anchor 12 has achieved the desired force against the vaginal wall as determined by the physician, the anchor 12 is thus "locked" in place in the deployed position within the vagina 5. In this way, the balloon 6 is retained in its proper position within the uterine cavity 4 by the anchor 12 resisting and even preventing displacement or dislodgement of the catheter 8 and the balloon 6 carried on the distal end thereof, allowing the apparatus 2 to function as intended for the control and management of PPH and uterine bleeding. Blood or other fluids within the uterus 4 may enter the openings 17 at the distal end 15 of the catheter 8 and drain through the drainage lumen 16 and/or the lumen of the stylet 10. The anchor 12 does not obstruct visualization of the cervix 7 and vagina 5 which allows continued monitoring of the tissues so that the physician may determine whether the bleeding has been controlled or stopped.

When release and removal of the anchor 12 is desired, the physician may grasp the proximal end(s) 40 of tethers 38 and pull down or proximally on the tethers 38. Preferably, if the one or more tethers 38 are directly secured to the outer disk 20, the physician may grasp one tether 38 so that pulling proximally causes the anchor 12 to tilt and take on an oval shape, as shown generally in FIGS. 5 and/or 9. Similarly, if the one or more tethers 38 are secured to one or more arms 33 extending from the inner clip 18, it is preferably that the physician grip and pull proximally on the tether 38 that extends from the arm 33 that is most proximally located. In other words, as shown in FIG. 6, one tether 38 is tied to the bend 31 of arm 33 at the lower-most portion of the outer disk 20 near second end 28. In this orientation, the physician would preferably pull upon this one tether 38 while leaving the other tether 38 (attached to the upper or distal most arm 33 near the first end 26 of the disk) hanging free.

Again, pulling the lower, most proximally located tether 38 taut, causes the anchor 12 to tilt slightly and take on an oval shape as the outer edges of the outer disk 20 move radially inwardly to thereby collapse the outer disk 20, which is conducive to removal. The reduction of the outer diameter of the outer disk 20 also allows the inner clip 18 to again release or relax its grip upon the underlying catheter shaft 9 to allow anchor 12 to dislodge from the vagina 5. The anchor may then slide backwards in a proximal direction along the catheter shaft 9, thus moving the anchor 12, including the outer disk 20 and inner clip 18, to release the anchor 12 from the cervix 7 and the vagina 5. If and when uterine bleeding is controlled, the balloon 6 may then be deflated and the tamponade assembly removed from the patient upon completion of the procedure. Preferably, the balloon could be deflated before the anchor 12 is removed to prevent premature displacement of the balloon 6 into the cervix 7. The stylet 10 may also be utilized to stabilize, support and/or guide the tamponade assembly 2 during removal from the patient.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A uterine tamponade assembly comprising: a catheter comprising a longitudinal body having a proximal end and a distal end and at least one drainage lumen extending there between; an expandable tamponade device located at the distal end of the catheter, the tamponade device configured for insertion into the body cavity; an anchor for securing the assembly within the body cavity, the anchor comprising: a clip, a first arm extending radially outwardly from the clip and a second arm extending radially outwardly from the clip, wherein the first and second arms each comprise a non-linear portion; and a resilient outer disk disposed about the clip, wherein the first arm is secured to the outer disk and wherein the outer disk comprises a hinge structure.

2. The assembly of claim 1 where in the tamponade device comprises an inflatable balloon configured for expansion within a body cavity.

3. The assembly of claim 1 wherein the outer disk is concentric with the clip.

4. The assembly of claim 1 wherein the anchor is configured for insertion and expansion in the cervix.

5. The assembly of claim 1 further comprising a stylet extending longitudinally within the drainage lumen of the catheter.

6. The assembly of claim 1 wherein the second arm being is located diametrically opposite the first arm about a circumference of the clip.

7. The assembly of claim 6 wherein the outer disk comprises a first opening configured to receive at least a portion of the first arm therein and a second opening configured to receive at least a portion of the second arm therein.

8. The assembly of claim 1 wherein the clip at least partially circumferentially surrounds the longitudinal body of the catheter.

9. The assembly of claim 1 wherein an inner surface of the clip comprises a gripping surface adapted to enhance traction between the inner surface of the clip and the longitudinal body of the catheter.

10. The assembly of claim 1 wherein the outer disk comprises at least one opening configured to receive at least a portion of the first arm therein.

11. The assembly of claim 1 wherein the hinge structure comprises at least one recess formed in a sidewall of the outer disk.

12. The assembly of claim 1 wherein a portion of the arm serves as a pivot point for the hinge structure.

13. The assembly of claim 1 wherein the hinge structure comprises a first hinge and a second hinge formed in the outer disk and wherein the first hinge and second hinge are located diametrically opposite each other.

14. A vaginal anchor for securing a balloon catheter in the uterine cavity, the vaginal anchor comprising: a clip, a first arm extending radially outwardly from the clip and a second arm extending radially outwardly from the clip, wherein the first and second arms each comprise a bent portion, and a resilient outer disk disposed about the clip, wherein the first arm is secured to the outer disk, and wherein the outer disk comprises a hinge structure.

15. The vaginal anchor of claim 14 wherein the outer disk is concentric with the clip.

16. The vaginal anchor of claim 14 wherein the sidewall of the outer disk flares radially outwardly from a second end to a first end.

17. The vaginal anchor of claim 14 wherein the sidewall of the outer disk comprises one or more apertures formed therein.

18. The vaginal anchor of claim 17 wherein at least one tether is threaded through at least one of the apertures formed in the sidewall of the outer disk.

19. The vaginal anchor of claim 14 further comprising multiple pairs of apertures formed in the sidewall of the outer disk and wherein one or more tethers are fastened to at least one of the multiple pairs of apertures.

20. The vaginal anchor of claim 14 wherein the second arm is located diametrically opposite the first arm about a circumference of the clip.

21. The vaginal anchor of claim 20 wherein the outer disk comprises a first opening configured to receive at least a portion of the first arm therein and a second opening configured to receive at least a portion of the second arm therein.

22. The vaginal anchor of claim 14 wherein the outer disk comprises at least one opening configured to receive at least a portion of the first arm therein.

23. The vaginal anchor of claim 14 wherein the hinge structure comprises at least one recess formed in a sidewall of the outer disk.

24. The vaginal anchor of claim 14 wherein the hinge structure is configured to allow a first portion of the outer disk pivot relative to a second portion of the outer disk.

25. The vaginal anchor of claim 14 wherein a portion of the first arm serves as a pivot point for the hinge structure.

26. The vaginal anchor of claim 14 wherein the hinge structure comprises a first hinge and a second hinge formed in the outer disk and wherein the first hinge and second hinge are located diametrically opposite each other.

27. The vaginal anchor of claim 14 wherein the outer disk is moveable from a first radially outwardly expanded configuration to a second collapsed configuration.

28. The vaginal anchor of claim 27 wherein the outer disk is biased in the first radially outwardly expanded configuration.

* * * * *